US009955241B2

(12) United States Patent
Smith

(10) Patent No.: US 9,955,241 B2
(45) Date of Patent: Apr. 24, 2018

(54) DEVICE IDENTIFICATION

(71) Applicant: Elekta Limited, West Sussex (GB)

(72) Inventor: Adrian Maxwell Smith, London (GB)

(73) Assignee: ELEKTA LIMITED, Sussex (GB)

( * ) Notice: Subject to any disclaimer, the term of this patent is extended or adjusted under 35 U.S.C. 154(b) by 0 days.

(21) Appl. No.: 15/437,672

(22) Filed: Feb. 21, 2017

(65) Prior Publication Data

US 2017/0245027 A1  Aug. 24, 2017

(30) Foreign Application Priority Data

Feb. 18, 2016 (GB) .................................. 1602849.0

(51) Int. Cl.
| G08B 21/00 | (2006.01) |
| H04Q 9/00 | (2006.01) |
| A61N 5/10 | (2006.01) |
| G06F 21/42 | (2013.01) |
| G06F 21/43 | (2013.01) |
| G06F 21/44 | (2013.01) |
| H04L 29/06 | (2006.01) |

(52) U.S. Cl.
CPC ............... *H04Q 9/00* (2013.01); *A61N 5/10* (2013.01); *G06F 21/42* (2013.01); *G06F 21/43* (2013.01); *G06F 21/44* (2013.01); *H04L 63/08* (2013.01); *H04L 63/18* (2013.01); *H04Q 2209/10* (2013.01); *H04Q 2209/30* (2013.01)

(58) Field of Classification Search
CPC ..................................................... G08B 21/182
USPC ......................................................... 340/626
See application file for complete search history.

(56) References Cited

U.S. PATENT DOCUMENTS

| 6,405,261 | B1 | 6/2002 | Gaucher |
| 7,444,409 | B2 | 10/2008 | Zou |
| 2002/0062407 | A1* | 5/2002 | Tateyama ............... G06F 3/1209 710/11 |
| 2005/0035861 | A1 | 2/2005 | Gliessmann et al. |
| 2007/0178882 | A1* | 8/2007 | Teunissen ............... H04L 63/18 455/411 |
| 2007/0249286 | A1* | 10/2007 | Ma ........................ G06F 19/327 455/41.3 |

(Continued)

FOREIGN PATENT DOCUMENTS

CA    2313118    6/1999

OTHER PUBLICATIONS

Extended Search Report for European Application No. 17156572.4 from the European Patent Office, dated Jul. 17, 2017.

(Continued)

*Primary Examiner* — Santiago Garcia

(74) *Attorney, Agent, or Firm* — Finnegan, Henderson, Farabow, Garrett & Dunner, L.L.P.

(57) ABSTRACT

An apparatus for enabling a first device to identify a second device comprises a first interface and a second interface. Each interface is configured to allow communication between the first device and the second device, and the first interface is distinct from the second interface. The apparatus further comprises one or more controllers configured to receive a first identifier from the second device via the first interface. If the first identifier has a predetermined value, the controllers receive a second identifier from the second device via the second interface. The controllers identify the second device using the second identifier.

20 Claims, 3 Drawing Sheets

(56) References Cited

U.S. PATENT DOCUMENTS

| | | | |
|---|---|---|---|
| 2008/0255782 A1* | 10/2008 | Bilac | H02J 13/001 |
| | | | 702/62 |
| 2009/0215398 A1* | 8/2009 | Adler | H04L 63/08 |
| | | | 455/41.3 |
| 2012/0163538 A1 | 6/2012 | Henning | |
| 2012/0297458 A1 | 11/2012 | Tom | |
| 2013/0060969 A1 | 3/2013 | Ylikoski et al. | |
| 2014/0295761 A1 | 10/2014 | Lo | |
| 2015/0025548 A1* | 1/2015 | Franklin | A61B 90/14 |
| | | | 606/130 |
| 2015/0161835 A1* | 6/2015 | Jablokov | G07C 9/00111 |
| | | | 340/5.61 |
| 2016/0029890 A1* | 2/2016 | Stump | A61B 5/0022 |
| | | | 600/301 |
| 2016/0381699 A1* | 12/2016 | Rubin | H04L 67/2809 |
| | | | 370/329 |
| 2017/0031337 A1* | 2/2017 | Jablokov | G08C 17/02 |
| 2017/0195754 A1* | 7/2017 | Grambichler | H04L 7/0091 |

OTHER PUBLICATIONS

Elekta Limited: "Corrective Maintenance Manual—Accessories", Elekta Digital Linear Accelerator, Publication date: Sep. 2012 (136 pages).

\* cited by examiner

DEVICE IDENTIFICATION

CROSS-REFERENCE TO RELATED PATENT APPLICATIONS

This application claims the benefit and priority of prior United Kingdom Patent Application No. 1602849.0, filed on Feb. 18, 2016, the entire contents of which are incorporated by reference herein.

TECHNICAL FIELD

The present disclosure generally relates to apparatuses and methods for enabling a device to identify another device. Examples of the disclosure include, without limitation, apparatuses and methods for enabling a radiotherapy device to identify an accessory connected thereto.

BACKGROUND

Radiotherapy is a technique for killing cancerous cells with ionising radiation. The ionising radiation is generated by a radiotherapy device such as a linear accelerator. Such radiotherapy devices typically comprise a multileaf collimator (MLC), which shapes a radiation beam in order to suit a particular patient's clinical need. It is known to attach additional devices, referred to herein as accessories, to radiotherapy devices in order to provide finer control over the shape of the radiation beam. Examples of accessories that are commonly attached to radiotherapy devices include electron applicators, cones, shadow trays and secondary MLCs.

An electron applicator comprises a plurality of planar layers of a radiation-absorbing material, wherein each layer has an aperture through which the radiation beam can pass. In use, an electron applicator is positioned within the radiation beam, such that the beam passes through the aperture of each layer before reaching the patient. Electron applicators provide additional collimation to the beam, and also reduce the patient's exposure to scattered electrons and secondary radiation. Electron applicators having apertures of different sizes and shapes are available, such that an electron applicator having a size and shape that is most suited to a given patient is selected and attached to the radiotherapy device.

A cone is a block of a radiation-absorbing material comprising a bore through which the radiation beam can pass. In use, a cone is positioned within the radiation beam, such that the beam passes through the bore before reaching the patient. The bore further collimates the beam, such that the diameter of the beam when it emerges from the cone corresponds to the diameter of the bore. Cones having bores of different diameters are available, such that the cone that is best suited to a particular patient is selected and attached to the radiotherapy device.

A shadow tray is a tray positioned between the radiotherapy device and a patient. One or more blocks of a radiation-absorbing material, such as lead, are placed on the tray in order to prevent certain portions of the radiation beam from reaching the patient. The radiation beam is thus shaped according to the position of the blocks on the shadow tray.

A secondary MLC is similar to the MLC that is typically already present on a radiotherapy device such as a linear accelerator. The secondary MLC supplements the collimation that is provided by the radiotherapy device's own MLC.

The accessory that is used for a radiotherapy session is chosen by a clinician to suit a particular patient's clinical need. Care must be taken to attach the correct accessory to the radiotherapy device before each radiotherapy session, because an incorrect accessory could result in the patient being exposed to an inappropriately-shaped beam or an inappropriate radiation dose.

To ensure patient safety, the Elekta™ Digital Linear Accelerator comprises an interface that is capable of identifying an accessory that is attached thereto. This interface is described in the "*Elekta Digital Linear Accelerator Corrective Maintenance Manual—Accessories*" (Elekta Limited, 2012), which is incorporated by reference herein in its entirety. The interface comprises a twenty-four pin Centronics connector. Seven pins of the connector are assigned to carrying a seven-bit code for identifying an electron applicator that is attached to the linear accelerator. Another two pins of the connector are assigned to carrying a two-bit code that allows the linear accelerator to identify whether an electron applicator or a shadow tray is connected thereto. However, the limited number of pins that is available on the connector places an upper limit on the number of different accessories that can be identified via the interface.

SUMMARY

Disclosed herein is an apparatus and method for enabling a device to identify another device. Particular examples of the disclosure enable a radiotherapy device to identify a greater number of accessories than is otherwise possible with the radiotherapy device's existing interface.

In accordance with a first aspect, an apparatus for enabling a first device to identify a second device is provided. The apparatus comprises a first interface and a second interface, each interface configured to allow communication between the first device and the second device, wherein the first interface is distinct from the second interface. The apparatus further comprises one or more controllers configured to: receive a first identifier from the second device via the first interface; determine whether the first identifier has a predetermined value; upon determining that the first identifier has the predetermined value, receive a second identifier from the second device via the second interface; and identify the second device using the second identifier.

The one or more controllers may be further configured to authenticate the second device by sending an authentication code to the second device via the second interface, and receiving the authentication code from the second device via the first interface. The first interface may be configured to allow communication between the first device and the second device via an electrical connection between the first and second devices. The one or more controllers may be further configured to control the functionality of the second device by sending data to the second device via the second interface. The second interface may be configured to allow communication between the first device and the second device via a wireless communication link between the first and second devices. The apparatus may be further configured to extract the second identifier from a signal that is repeatedly broadcast by the second device.

In accordance with another aspect, an apparatus for enabling a second device to identify itself to a first device is provided. The apparatus comprises a first interface and a second interface, each interface configured to allow communication between the first device and the second device, wherein the first interface is distinct from the second interface. The apparatus further comprises one or more controllers configured to: send a first identifier to the first device via the first interface, wherein the first identifier has a predetermined value; and send a second identifier to the first device via the second interface, wherein the second identifier has a value that identifies the second device.

The apparatus may be further configured to receive an authentication code from the first device via the second interface, and send the authentication code to the first device via the first interface. The first interface may be configured to allow communication between the first device and the second device via an electrical connection between the first and second devices. The one or more controllers may be further configured to: receive data for controlling the functionality of the second device from the first device via the second interface; and control the functionality of the second device in accordance with the received data. The second interface may be configured to allow communication between the first device and the second device via a wireless communication link between the first and second devices. The second interface may be configured to broadcast the second identifier repeatedly.

In accordance with another aspect, a method for enabling a first device to identify a second device is provided. The method is performed at the first device, which comprises a first interface and a second interface, each interface configured to allow communication between the first device and the second device, wherein the first interface is distinct from the second interface. The method comprises: receiving a first identifier from the second device via the first interface; determining whether the first identifier has a predetermined value; upon determining that the first identifier has the predetermined value, receiving a second identifier from the second device via the second interface; and identifying the second device using the second identifier.

The method may further comprise authenticating the second device by sending an authentication code to the second device via the second interface, and receiving the authentication code from the second device via the first interface. The first interface may be configured to allow communication between the first device and the second device via an electrical connection between the first and second devices. The method may further comprise controlling the functionality of the second device by sending data to the second device via the second interface. The second interface may be configured to allow communication between the first device and the second device via a wireless communication link between the first and second devices. The method may further comprise extracting the second identifier from a signal that is repeatedly broadcast by the second device.

In accordance with another aspect, a method for enabling a second device to identify itself to a first device is provided. The method is performed at the second device, which comprises a first interface and a second interface, each interface configured to allow communication between the first device and the second device, wherein the first interface is distinct from the second interface. The method comprises: sending a first identifier to the first device via the first interface, wherein the first identifier has a predetermined value; and sending a second identifier to the first device via the second interface, wherein the second identifier has a value that identifies the second device.

The method may further comprise: receiving an authentication code from the first device via the second interface; and sending the authentication code to the first device via the first interface. The first interface may be configured to allow communication between the first device and the second device via an electrical connection between the first and second devices. The method may further comprise: receiving data for controlling the functionality of the second device from the first device via the second interface; and controlling the functionality of the second device in accordance with the received data. The second interface may be configured to allow communication between the first device and the second device via a wireless communication link between the first and second devices. The method may further comprise repeatedly broadcasting the second identifier via the second interface.

In accordance with another aspect, an apparatus for enabling a first device to authenticate a second device is provided. The apparatus comprises a first interface and a second interface, each interface configured to allow communication between the first device and the second device, wherein the first interface is distinct from the second interface. The apparatus further comprises one or more controllers configured to: send an authentication code to the second device via the second interface; receive a response from the second device via the first interface; and authenticate the second device by comparing the authentication code with the response. The one or more controllers may be configured to determine that the second device is authentic when the response is equal to the authentication code.

In accordance with another aspect, an apparatus for enabling a second device to be authenticated by a first device is provided. The apparatus comprises a first interface and a second interface, each interface configured to allow communication between the first device and the second device, wherein the first interface is distinct from the second interface. The apparatus further comprises one or more controllers configured to: receive an authentication code from the first device via the second interface; and send a response to the first device via the first interface. The response may comprise the authentication code received from the first device.

In accordance with another aspect, a method for enabling a first device to authenticate a second device is provided. The method is performed at the first device, the first device comprising a first interface and a second interface, each interface configured to allow communication between the first device and the second device, wherein the first interface is distinct from the second interface. The method comprises: sending an authentication code to the second device via the second interface; receiving a response from the second device via the first interface; and authenticating the second device by comparing the authentication code with the response. The method may further comprise determining that the second device is authentic when the response is equal to the authentication code.

In accordance with another aspect, a method for enabling a second device to be authenticated by a first device is provided. The method is performed at the second device, the second device comprising a first interface and a second interface, each interface configured to allow communication between the first device and the second device, wherein the first interface is distinct from the second interface. The method comprises: receiving an authentication code from the first device via the second interface; and sending a response to the first device via the first interface. The response may comprise the authentication code received from the first device.

A further aspect provides a processor-readable medium comprising instructions which, when executed by a processor, cause the processor to perform any of the methods as previously described.

In accordance with any of the preceding aspects, the first device may be a radiotherapy device and the second device may be an accessory for attachment to the radiotherapy device.

BRIEF DESCRIPTION OF THE DRAWINGS

Embodiments will now be described, purely by way of example, with reference to the accompanying drawings, wherein like elements are indicated using like reference signs, and in which.

DETAILED DESCRIPTION

Figure 1:
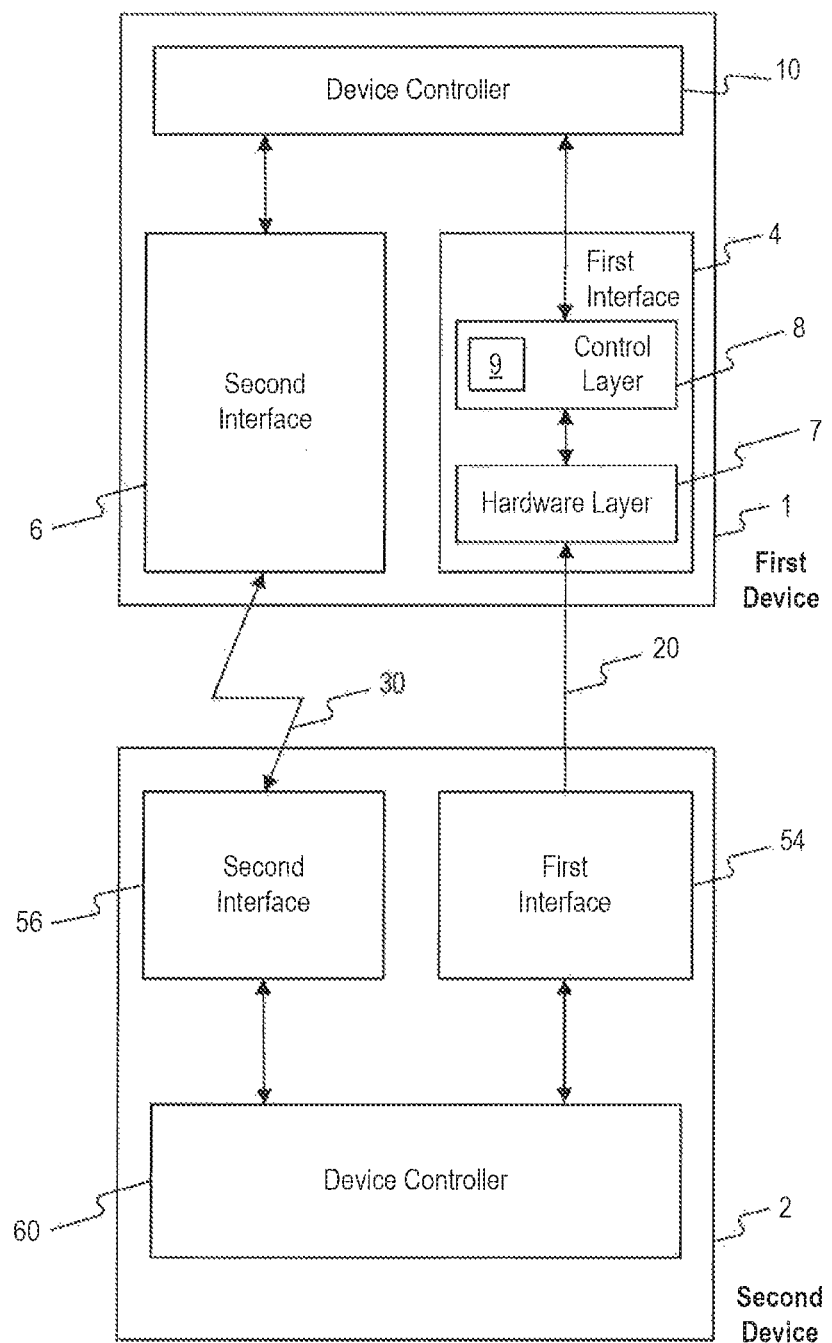
FIG. 1 is a schematic diagram of a first device attached to a second device.

FIG. 1 is a schematic diagram of a first device 1 attached to a second device 2. The first device 1 may be a radiotherapy device, such as a linear accelerator. The second device 2 may be an accessory for attachment to a radiotherapy device. For example, the second device 2 may be an electron applicator, a cone, a shadow tray or a secondary MLC. However, it will be appreciated that the present disclosure is not limited to the field of radiotherapy, and that the apparatuses and methods disclosed herein can be used to enable any suitable first device 1 to identify any suitable second device 2.

The first device 1 comprises a first interface 4, a second interface 6 and a device controller 10. The second device 2 also comprises a first interface 54, a second interface 56 and a device controller 60. The first interface 4 of the first device 1 is compatible with the first interface 54 of the second device 2, such that the first interfaces 4, 54 enable communication between the first and second devices 1, 2. Similarly, the second interface 6 of the first device 1 is compatible with the second interface 56 of the second device 2, such that the second interfaces 6, 56 enable communication between the first and second devices 1, 2. The first interfaces 4, 54 are distinct from the second interfaces 6, 56. That is, the functionality of the first interfaces 4, 54 is independent of the functionality of the second interfaces 6, 56. The first interfaces 4, 54 thus provide a first communication link 20 between the first and second devices 1, 2, whilst the second interfaces 6, 56 provide a second communication link 30 between the first and second devices 1, 2. The first and second communication links 20, 30 are separate from, and independent of, each other.

The first interfaces 4, 54 may be wired interfaces. More specifically, the first interfaces 4, 54 may allow communication via an electrical connection between the first device 1 and the second device 2. In an example, the first interfaces 4, 54 may be respective portions of an Elekta™ Digital Linear Accelerator accessory interface, as described above. In this example, the first interfaces 4, 54 provide unidirectional communication, such that the first device 1 (e.g. a radiotherapy device) can receive data that is sent from the second device 2 (e.g. an accessory for the radiotherapy device). However, it will be appreciated that the first interfaces 4, 54 may be implemented in any other suitable manner. For example, the first interfaces 4, 54 may be wireless interfaces and/or the first interfaces 4, 54 may allow bidirectional communication between the first device 1 and the second device 2. For the sake of simplicity, it will be assumed that the first interfaces 4, 54 are wired interfaces in the following description.

The second interfaces 6, 56 may be wired or wireless interfaces. If the second interfaces 6, 56 are wireless interfaces, they may be implemented using any suitable wireless communication technology. For example, the second interfaces 6, 56 may be configured to communicate using IEEE 802.11 (Wi-Fi™), Bluetooth™ or ZigBee™ communication protocols. Other suitable communication protocols could alternatively or additionally be used. In an example, the second interfaces 6, 56 are configured to communicate using the Bluetooth™ LE protocol (also known as Bluetooth™ Smart). The Bluetooth™ LE protocol is well-suited for use in the second interfaces 6, 56 because it has the ability to broadcast a beacon signal that comprises a Universally Unique Identifier (UUID), as will be discussed in more detail below.

The first interfaces 4, 54 and/or the second interfaces 5, 56 may comprise an optical interface. The optical interface may comprise a waveguide, such as an optical fibre. Alternatively, the optical interface may comprise an optical wireless communication (OWC) interface, such as a light fidelity (Li-Fi) interface.

The first interface 4 of the first device 1 comprises a hardware layer 7 and a control layer 8. The hardware layer 7 comprises electrical components that are configured to send and/or receive data via the first communication link 20. The hardware layer 7 may further comprise electrical components that are configured to detect when the second device 2 is attached to the first interface 4. The hardware layer 7 may further comprise electrical components that are configured to supply power to the second device 2, when the second device is attached to the first interface 4. The control layer 8 is configured to control the operation of the hardware layer 7. The control layer 8 may comprise a processor 9 that is coupled to a memory (not shown in FIG. 1). The memory stores instructions that, when executed by the processor 9, cause the processor to control the operation of the hardware layer 7. For example, when the hardware layer 7 receives data from the second device 2 via the first communication link 20, the control layer 8 may forward that data to another entity, such as the device controller 10. The operations performed by the hardware layer 7 and the control layer 8 are discussed in more detail below with reference to FIGS. 2 and 3. It will be understood by those skilled in the art that the references to a hardware layer 7 and a control layer 8 are merely a way of describing the functionality of the first interface 4, and do not imply a particular hardware implementation.

The first interface 54 of the second device 2 can be similar to the first interface 4 of the first device 1 and, therefore, is not described in detail.

The device controller 10 of the first device 1 is configured to identify the second device 2. To this end, the device controller 10 is configured to communicate with the first interface 4 and the second interface 6 of the first device 1. The device controller 60 of the second device 2 is configured to perform operations that allow the second device 2 to identify itself to the first device 1. The device controller 60 is configured to communicate with the first interface 54 and the second interface 56 of the second device 2. When the second device 2 has been identified, the device controllers 10, 60 may be configured to communicate with one another via the first communication link 20 and/or the second communication link 30. For example, the device controllers 10, 60 may communicate in order to authenticate the second device 2. As another example, the device controllers 10, 60 may communicate in order that the first device 1 can control the functionality of the second device 2. As yet another example, the device controllers 10, 60 may communicate in order that the first and second devices 1, 2 can exchange data.

Each device controller 10, 60 may comprise a processor that is coupled to a respective memory (not shown in FIG. 1). Each memory stores instructions that, when executed by the respective processor, cause the processor to perform the operations described below with reference to FIGS. 2 and 3. As shown in FIG. 1, the device controllers 10, 60 can be embedded systems that are housed within the first and second devices 1, 2 respectively. If the device controller 10 is an embedded system, it is possible for a single processor to perform the operations of both the device controller 10 and the control layer 8. However, either or both of the device controllers 10, 60 may be general purpose computer systems that are separate from the first and second devices 1, 2; in this case, each device controller 10, 60 can communicate with the respective device 1, 2 via a communication network.

Figure 2:
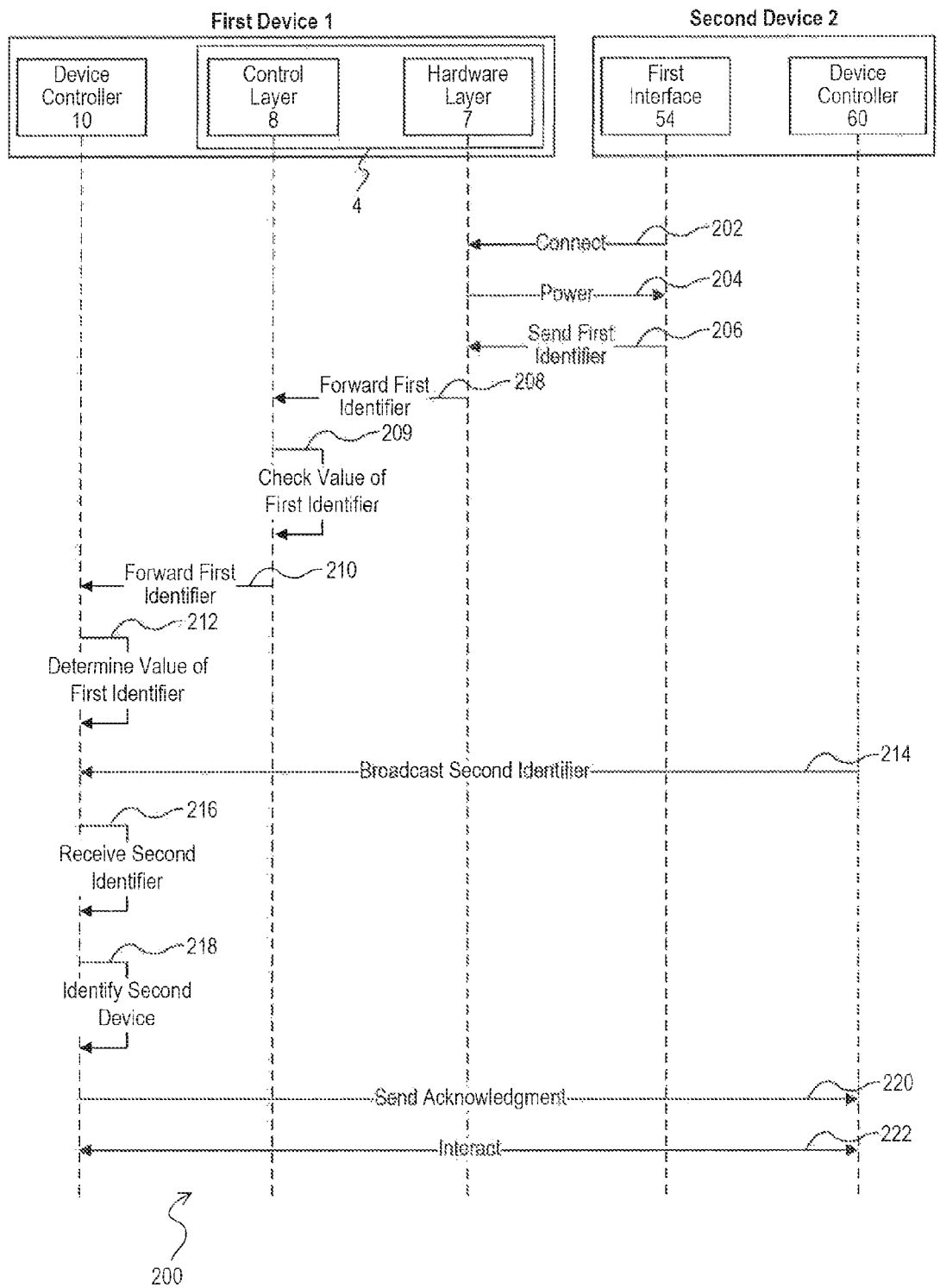
FIG. 2 is a sequence diagram of a method of enabling the first device to identify the second device.

The operation of the first device 1 and the second device 2 will now be described with reference to FIG. 2, which illustrates a method 200 for enabling the first device 1 to identify the second device 2.

At step 202, the first interface 54 of the second device 2 is connected to the first interface 4 of the first device 1. Step 202 may include, for example, inserting a plug on one device into a socket on the other device, or connecting a cable between the devices 1, 2. Connecting the first interfaces 4, 54 in this manner creates an electrical connection between the first device 1 and the second device 2, thereby providing the first communication link 20.

The second communication link 30 may be established before, after, or at the same time as step 202 is performed. For example, if the second interfaces 6, 56 are wireless interfaces, the second communication link can be established when the first device 1 and second device 2 are brought into communication range of each other, and the method 200 may subsequently be performed. In another example, the second communication link 30 can be established in response to the establishment of the first communication link 20 at step 202.

At step 204, the first device 1 supplies power to the second device 2. The power may be supplied via the first interfaces 4, 54, or it may be supplied via another electrical connection (not shown in FIG. 1) between the devices 1, 2. Step 204 may be performed in response to the first device 1 detecting that the second device 2 was connected at step 202. Step 204 is optional, as it is possible for the second device 2 to have its own power supply, such that it does not require power from the first device 1.

At step 206, the second device 2 sends a first identifier to the first device 1 via the first interfaces 4, 54. The first identifier is subsequently received by the hardware layer 7 of the first interface 4 of the first device 1. The first identifier has a predetermined value that indicates that the second device 2 will send a second identifier via the second interfaces 6, 56 (as described at step 214). The predetermined value may be selected from a plurality of predetermined values, each of which indicates that the second device 2 will send a second identifier via the second interfaces 6, 56. The plurality of predetermined values may optionally comprise a range of consecutive values.

Step 206 may comprise the second device 2 applying a voltage to one or more conductors that form the first communication link 20. For example, the second device 2 may apply a digital voltage level to each of a plurality of conductors, such that a word is formed by the combination of digital voltage levels on the plurality of conductors. In this example, the first identifier is the value of the word. As another example, the second device 2 may apply a time-varying digital voltage level to a conductor, such that a word is formed by the digital voltage levels that are applied over a predefined period of time. In this example, the first identifier is the value of the word. As yet another example, the second device 2 may apply an analogue voltage to a conductor, where the amplitude of the analogue voltage represents the first identifier.

In an example in which the first interfaces 4, 54 are respective portions of an Elekta™ Digital Linear Accelerator accessory interface, step 206 comprises the second device 2 applying a digital voltage level to the pins that are assigned to identifying an electron applicator. Hence, the second device 2 can send the first identifier to the first device 1 by applying a "high" or "low" digital voltage level to specific pins. For example, to send a first identifier with a value of zero (i.e. a binary value of 0000000), the second device 2 applies a "low" voltage level to all seven pins of the connector that are assigned to identifying an electron applicator. As another example, to send a first identifier with a value of seven (i.e. a binary value of 0000111), the second device 2 applies a "low" voltage level to the four highest-order pins and a "high" voltage level to the three lowest-order pins. The specification for the Elekta™ Digital Linear Accelerator accessory interface defines a number of "reserved" values for those seven pins that are not used for any purpose. The predetermined value of the first identifier may be one of the reserved values. The use of a reserved value allows new accessories to be identified in accordance with the identification method 200 disclosed herein, without affecting the operation of older accessories that are not configured to perform the method 200.

At step 208, the hardware layer 7 forwards the first identifier to the control layer 8 of the first interface 4 of the first device 1.

At step 209, the control layer 8 checks the value of the first identifier. Step 209 may include the control layer 8 determining whether the value of the first identifier is equal to the predetermined value. As mentioned above, the predetermined value indicates that the second device 2 will send a second identifier via the second interfaces 6, 56. The control layer 8 may, for example, compare the value of the first identifier with a look-up table or the contents of a processor register to determine whether the first identifier is equal to the predetermined value. As explained in connection with step 206, the predetermined value of the first identifier may be selected from a plurality of predetermined values, in which case the control layer 8 determines whether the value of the first identifier is equal to any of the plurality of predetermined values. When the control layer 8 determines that the value of the first identifier is equal to the predetermined value, or any of the plurality of predetermined values, the control layer 8 proceeds to perform step 210.

If the value of the first identifier is not equal to the predetermined value, or any of the plurality of predetermined values, step 209 may further include the control layer 8 determining whether the value of the first identifier identifies the second device 2. For example, the control layer 8 may determine whether the value of the first identifier is equal to any of the values in a second look-up table. The second look-up table comprises a plurality of possible values of the first identifier, each of which is associated with information that identifies a respective second device 2. Thus, the control layer 8 is able to identify the second device 2 when the value of the first identifier is equal to a value in the second look-up table and, if so, the method 200 terminates. The second look-up table can thus provide backwards-compatibility with second devices 2 that are not capable of sending a second identifier via the second interfaces 6, 56, by allowing those second devices 2 to be identified by the value of the first identifier alone.

If the value of the first identifier is not equal to the predetermined value or to a value in the second look-up table, step 209 may further include the control layer 8 determining that the second device 2 is incompatible with the first device 1. The control layer 8 may optionally notify the device controller 10 of the first device 1 of the incompatibility of the second device 2, which may assist with troubleshooting. The method 200 then terminates.

It will be appreciated that step 209 may be omitted, such that the control layer 8 proceeds from step 208 to step 210 without checking the value of the first identifier. In this case, the device controller 10 may determine whether the value of the first identifier identifies the second device 2, as described above in connection with step 209. However, performing step 209 can allow certain second devices 2 to be identified more quickly, and allow incompatible second devices 2 to be rejected more quickly.

At step 210, the control layer 8 forwards the first identifier to the device controller 10 of the first device 1. The first identifier is thus received by the device controller 10 of the first device 1.

In an alternative embodiment, step 210 comprises the control layer 8 notifying the device controller 10 to monitor the second interface 6 for a second identifier. In this embodiment, the control layer 8 does not forward the first identifier to the device controller 10, and only the control layer 8 determines whether the first identifier has the predetermined value or any of the plurality of predetermined values. In this embodiment, step 212 (discussed below) is not performed and the method proceeds to step 214. At step 212, the device controller 10 determines whether the value of the first identifier is equal to the predetermined value. As mentioned above, the predetermined value indicates that the second device 2 will send a second identifier via the second interfaces 6, 56. For example, the device controller 10 may compare the value of the first identifier with a third look-up table or the contents of a processor register to determine whether the first identifier is equal to the predetermined value. When the device controller 10 determines that the value of the first identifier is equal to the predetermined value, the device controller 10 proceeds to perform step 216. As explained in connection with step 206, the predetermined value of the first identifier may be selected from a plurality of predetermined values. In this case, step 212 comprises the device controller 10 determining whether the value of the first identifier is equal to any of the plurality of predetermined values.

Meanwhile, at step 214, a second identifier is communicated from the second device 2 to the first device 1 via the second interfaces 6, 56. The second identifier has a value that identifies the second device 2. For example, the value of the second identifier can indicate what type of accessory the second device 2 is, e.g. an electron applicator, a cone, a shadow tray, a secondary MLC or another type of accessory. The value of the second identifier may optionally also indicate one or more properties of the second device 2. For example, if the second device 2 is an electron applicator, the second identifier can indicate the size and/or shape of the aperture of the electron applicator. The second identifier may optionally also include data, such as a serial number, that uniquely identifies the second device 2.

In an example in which the first and second interfaces 6, 56 are wireless interfaces, step 214 comprises the device controller 60 of the second device 2 instructing the second interface 56 to broadcast the second identifier. The second identifier may be broadcast repeatedly. The second device 2 may begin to broadcast the second identifier before it is connected to the first device 1 at step 202. Alternatively, the second device 2 may begin to broadcast the second identifier when it sends the first identifier at step 206, or shortly thereafter. In an example in which the second interfaces 6, 56 are configured to communicate using the Bluetooth™ LE protocol, the second identifier can be included in a beacon signal defined by that protocol. For example, the second identifier can be included in the UUID field of the Bluetooth™ LE beacon signal. The beacon signals defined by other communication protocols may also be used to broadcast the second identifier, and the second identifier may be embedded in any suitable field of those beacon signals. The use of a beacon signal provides an easily-implemented method of broadcasting the second identifier repeatedly.

Optionally, step 214 may be performed in response to the second device 2 receiving a signal from the first device 1. For example, the first device 1 may send a signal (not shown in FIG. 2) to the second device 2 after it has determined that the value of the first identifier is equal to the predetermined value at step 212. This signal may be sent via either the first interfaces 4, 54 or the second interfaces 6, 56. In response to receiving the signal from the first device 1, the second device 2 may start communicating the second identifier to the first device 1.

At step 216, the second identifier is received by the first device 1 via the second interface 6. Continuing the previously-mentioned example in which the first and second interfaces 6, 56 are wireless interfaces, step 216 comprises the device controller 10 of the first device 1 monitoring the data that is received via the second interface 6 to determine whether it contains data that might be a second identifier. For example, the device controller 10 may determine whether the second interface 6 has received a beacon signal. If so, the second identifier is extracted from the beacon signal, and subsequently used to identify the second device 2 at step 218. For example, if the second interface 6 has received a Bluetooth™ LE beacon signal, the device controller 10 reads the UUID field of the beacon signal, and subsequently uses the UUID to identify the second device 2. The device controller 10 begins monitoring the second interface 6 for the presence of a second identifier in response to determining that the value of the first identifier was equal to the predetermined value at step 212.

At step 218, the first device 1 identifies the second device 2 using the second identifier. For example, the device controller 10 may search a data structure to find an entity that matches the second identifier that was received at step 216. An entity in the data structure may be considered to match the second identifier if it has a value that is equal to the second identifier, or if it has a value that is equal to a portion of the second identifier. If an entity in the data structure matches the second identifier, the device controller may retrieve additional information from that entity. The additional information can then be used to identify the second device. For example, the additional information can indicate what type of accessory the second device 2 is, and may optionally indicate one or more properties of the second device 2. In one example, the data structure is a look-up table, and the device controller 10 is configured to compare the received second identifier against a unique key in the look-up table. Upon finding a unique key that matches the received second identifier, the device controller 10 is configured to retrieve additional information from the row of the look-up table that contains the matching unique key.

If the first device 1 successfully identifies the second device 2 using the second identifier at step 218, the method proceeds to step 220. Otherwise, the method may return to step 216, whereupon the device controller 10 resumes monitoring the data that is received via the second interface 6 to determine whether it contains data that might be a second identifier.

At step 220, the first device 1 optionally sends an acknowledgement to the second device 2 via the second interfaces 6, 56. The acknowledgement indicates that the first device 1 has successfully identified the second device 2. Upon receiving the acknowledgement, the second device 2 may stop communicating the second identifier. Alternatively, rather than sending an acknowledgement at step 220, the method 300 illustrated in FIG. 3 may optionally be performed to enable the first device 1 to authenticate the second device 2.

At step 222, the first device 1 interacts with the second device 2. For example, the first and second devices 1, 2 may exchange information via the second interfaces 6, 56.

Step 222 may comprise the first device 1 transmitting information to the second device 2 via the second interfaces 6, 56. The ability for the first device 1 to transmit information to the second device 2 via the second interfaces 6, 56 is advantageous when the first interfaces 4, 54 are only capable of unidirectional communication from the second device 2 to the first device 1 (as is the case when the first interfaces 4, 54 are respective portions of an Elekta™ Digital Linear Accelerator accessory interface). For example, the second interfaces 6, 56 can allow the first device 1 to control the second device 2, which would otherwise not be possible when the first interfaces 4, 54 are unidirectional. More specifically, the first device 1 can send data for controlling the functionality of the second device 2 via the second interfaces 6, 56. The device controller 60 of the second device 2 can then control the functionality of the second device 2 in accordance with the received data.

The ability for the first device 1 to control the second device 2 is useful in embodiments in which the first device 1 is a radiotherapy device. For example, the radiotherapy device may control the position of a secondary MLC that is attached thereto. The radiotherapy device may also control other types of accessories via the second interfaces 6, 56. This can allow the radiotherapy device to optimise the radiation dose that is delivered during a radiotherapy session, for example by controlling an accessory to adjust the shape, size and/or direction of a radiation beam.

Communication via the second interfaces 6, 56 can be beneficial even when the first interfaces 4, 54 are capable of bidirectional communication. For example, the second interfaces 6, 56 may provide a higher bit rate than the first interfaces 4, 54.

Communication via the second interfaces 6, 56 can enable the communication of information that is not supported by the communication protocol of the first interfaces 4, 54. For example, in an embodiment in which the first device 1 is a radiotherapy device, communication via the second devices 6, 56 can allow new types of accessory to be attached thereto. As another example, communication via the second interfaces 6, 56 can allow the radiotherapy device to retrieve information from an accessory. The information retrieved from the accessory may include a serial number, a part number and/or a calibration date. This information can be used to automatically record the accessory that was connected to the radiotherapy device during a particular radiotherapy session.

The content of the information that the first device 1 sends to the second device 2 at step 222 can be selected according to the identity of the second device 2 that was determined at step 218. For example, the first device 1 may tailor the content of the information depending upon what type of accessory the second device 2 is and/or the properties of the second device 2. Similarly, the first device 1 may interpret the information that is received from the second device 2 at step 222 according to the identity of the second device 2 that was determined at step 218.

In the light of the foregoing description, those skilled in the art will appreciate that the method 200 can enable a first device (e.g. a radiotherapy device) to identify a greater number of second devices (e.g. accessories) than is otherwise possible with the first device's first interface 4. This is achieved by causing the second device 2 to send a first identifier to the first device 1 via the first interfaces 4, 54, where the first identifier has a predetermined value that indicates that the second device 2 will send a second identifier via the second interfaces 6, 56. The second identifier has a value that identifies the second device 2. Whereas the number of second devices 2 that can be uniquely identified with the first interfaces 4, 54 may be limited by the number of pins that is available on the first interfaces' connectors, the number of second devices 2 that can be identified by a second identifier sent via the second interfaces 6, 56 is not so limited. A greater number of second devices can thus be identified. Furthermore, the second identifier may include data, such as a serial number, that allows each second device to be uniquely identified.

The identification method 200 has the additional advantage that it does not require the hardware layer 7 of the first interface 4 of the first device 1 to be modified. The method 200 can be implemented simply by adding a second interface 6 to the first device 1, and by updating the instructions that are executed by the control layer 8 and the device controller 10. The first device 1 can thus be easily upgraded to identify a greater number of second devices 2. Furthermore, this also ensures that the first device 1 remains backwards-compatible with second devices 2 that are not capable of performing the identification method 200.

Another advantage of adding a second interface 6 to the first device 1, whilst retaining an existing first interface 4, arises when the first interface is a wired interface. In this case, the first interface 4 can provide a safety interlocking mechanism in the event that the second device 2 is disconnected from the first device 1. If the second device 2 is disconnected, the first device can detect the absence of an electrical connection between the first and second devices 1, 2. In response, the first device 1 can deactivate some or all of its functionality. This can prevent a radiotherapy device applying radiation to a patient if an accessory accidentally becomes detached.

Figure 3:
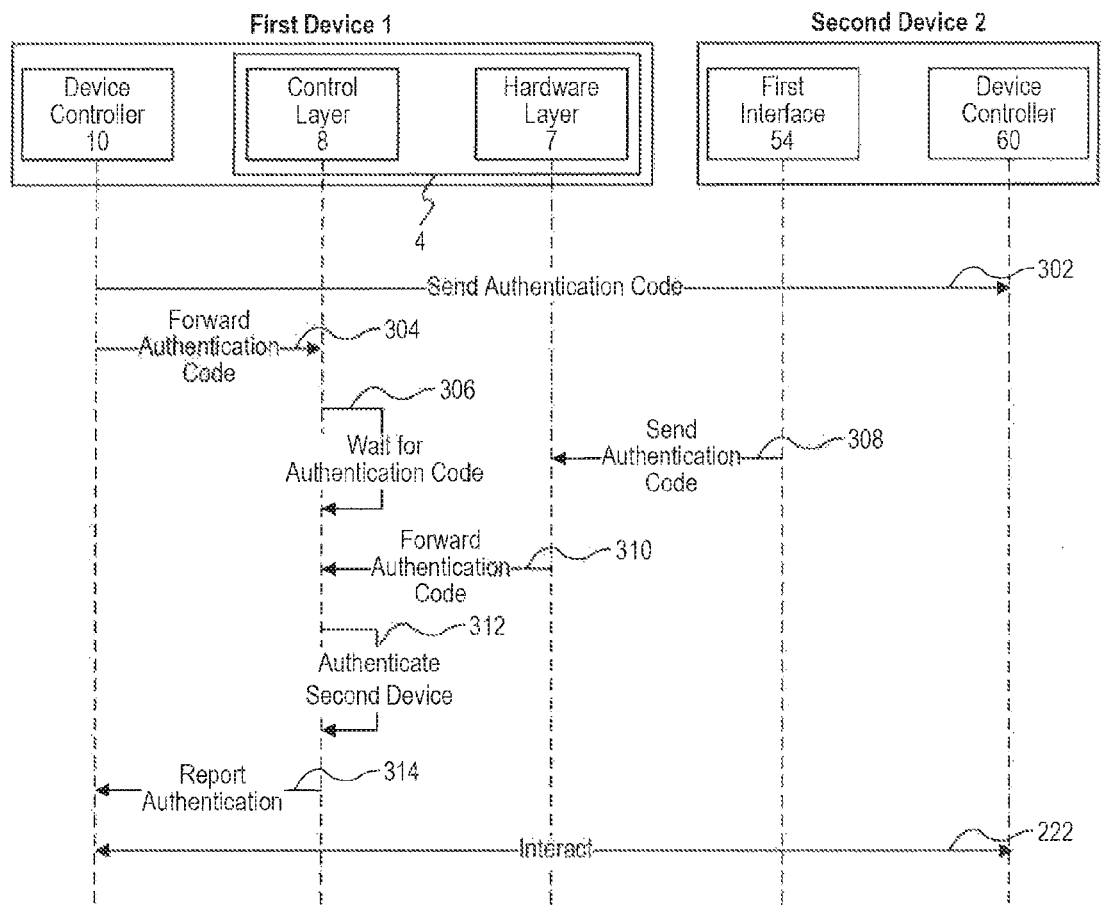
FIG. 3 is a sequence diagram of a method of enabling the first device to authenticate the second device.

A method 300 for enabling the first device 1 to authenticate the second device 2 will now be described with reference to FIG. 3. Whereas the purpose of the method 200 is to identify the second device 2, the purpose of the authentication method 300 is to determine whether the second device 2 is approved for use with the first device 1.

The method 300 begins at step 302, in which the first device 1 sends an authentication code to the second device 2 via the second interfaces 6, 56. The authentication code can be any numeric value that is capable of being communicated back to the first device 1 via the first interfaces 4, 54. For example, if the first interfaces 4, 54 are respective portions of an Elekta™ Digital Linear Accelerator accessory interface, in which seven pins are assigned to identifying an electron applicator, the authentication code can be any seven-bit binary value. The authentication code may be a random number generated by the device controller 10 of the first device 1. Generating the authentication code randomly can reduce the likelihood of successful authentication by an unapproved second device 2 that does not receive the authentication code sent at step 302.

In one implementation of step 302, the first device 1 sends the authentication code to the second device 2 in a beacon signal. For example, when the second interfaces 6, 56 are configured to communicate using the Bluetooth™ LE protocol, the authentication code can be included in a beacon signal defined by that protocol. For example, the authentication code can be included in the UUID field of the Bluetooth™ LE beacon signal. The use of a beacon signal provides an easily-implemented method of broadcasting the authentication code repeatedly. In another implementation of step 302, the first device 1 establishes a data connection with the second device 2 via the second interfaces 6, 56, and sends the authentication code to the second device 2 in any suitable format that is supported by that data connection. The data connection can be a point to point data connection and/or a bidirectional connection. The use of a bidirectional data connection can allow the first device 1 to receive an immediate acknowledgement, via the second interfaces 5, 56, that the authentication code was received by the second device 2. In contrast, when the authentication code is included in a beacon signal, the first device 1 may not expect to receive an acknowledgement from the second device 2 via the second interfaces 5, 56.

Step 302 may be performed immediately after the first device 1 sends an acknowledgement to the second device 2 at step 220 of method 200. Alternatively, step 302 may be performed instead of step 220, such that step 302 is performed immediately after the first device 1 identifies the second device 2 at step 218 of method 200.

As another alternative, step 302 may be performed immediately after step 212 of the identification method 200, and steps 214 to 222 of method 200 are performed only after the authentication method 300 has been completed. Thus, in this alternative, the second device 2 is identified only after it has been authenticated.

As yet another alternative, step 302 may be performed immediately after step 212 of the identification method 200, and steps 214 to 222 of method 200 are omitted. In this alternative, the first device 1 may use information other than the previously-mentioned second identifier to identify the second device 2. For example, if the first device 1 is a radiotherapy device, the device controller 10 of the first device 1 may refer to a treatment plan to identify the second device 2 that is connected thereto for the radiotherapy session that is in progress. As is known to those skilled in the art, a treatment plan is a set of instructions that defines how the radiotherapy device should apply radiation to a patient during a particular radiotherapy session.

As still another alternative, the authentication method 300 could be performed independently of the identification method 200, such that step 302 is not preceded by any of the steps of method 200.

At step 304, the device controller 10 of the first device 1 forwards the authentication code to the control layer 8 of the first interface 4. Upon receiving the authentication code, the control layer 8 waits to receive an authentication code from the hardware layer 7 at step 306.

Meanwhile, at step 308, the second device 2 sends the authentication code back to the first device 1 via the first interfaces 4, 54. Step 308 is performed in response to the second device 2 receiving the authentication code from the first device 1 via the second interfaces 6, 56. The authentication code is subsequently received by the hardware layer 7 of the first interface 4 of the first device 1.

The second device 2 may communicate the authentication code to the first device 1 in the same way as it sent the first identifier in step 206. For example, step 308 may comprise the second device 2 applying a voltage to one or more conductors that form the first communication link 20, such that a word is formed by the combination of digital voltage levels on the plurality of conductors. In this example, the authentication code is the value of the word. As another example, the second device 2 may apply a time-varying digital voltage level to a conductor, such that a word is formed by the digital voltage levels that are applied over a predefined period of time. In this example, the authentication code is the value of the word. As yet another example, the second device 2 may apply an analogue voltage to a conductor, where the amplitude of the analogue voltage represents the authentication code. In an example in which the first interfaces 4, 54 are respective portions of an Elekta™ Digital Linear Accelerator accessory interface, step 308 comprises the second device 2 applying a digital voltage level to the pins that are assigned to identifying an electron applicator. The received authentication code can thus be sent back to the first device 1 by setting appropriate pins to a "high" or "low" digital voltage level.

At step 310, the hardware layer 7 of the first interface 4 of the first device 1 forwards the first identifier to the control layer 8.

At step 312, the first device 1 authenticates the second device 2 by comparing the authentication code that was sent to the second device 2 with the authentication code that was received from the second device 2. More specifically, the control layer 8 compares the authentication code that was received from the device controller 10 at step 304 with the authentication code that was received from the hardware layer 7 at step 310. If the two authentication codes are equal, the second device 2 is successfully authenticated. That is, the second device 2 is assumed to be approved for use with the first device 1 because it has returned the authentication code. On the other hand, if the two authentication codes are not equal, the second device 2 fails the authentication process. That is, the second device 2 is assumed not to be approved for use with the first device 1 because it did not return the authentication code.

At step 314, the control layer 8 reports the outcome of the authentication step 312 to the device controller 10. For example, the control layer 8 may send a message to the device controller 10 that indicates whether the second device 2 was successfully authenticated or failed authentication. If the second device 2 was successfully authenticated, the method proceeds to step 222 in which the first device 1 interacts with the second device 2. Step 222 was previously described in the context of the method 200 shown in FIG. 2. If the second device 2 failed authentication, the device controller 10 may disable some or all of the functionality of the first device 1. In some examples, if the second device 2 failed authentication, steps 302 to 314 may be repeated until the second device 2 is successfully authenticated or until a maximum number of repetitions has been performed. If the second device 2 has still not been successfully authenticated after the maximum number of repetitions has been performed, the device controller 10 may disable some or all of the functionality of the first device 1.

Further steps could be added to the authentication method 300 in order to reduce the likelihood of an unapproved second device 2 being successfully authenticated. For example, steps 302 to 314 may be repeated one or more times, with the first device 1 sending a different authentication code at each repetition. Repeating the authentication process in this manner can reduce the probability of the second device 2 sending the correct authentication code by chance.

Cryptography may be used to reduce the likelihood of an unapproved second device 2 being successfully authenticated. For example, the first device 1 can encrypt the authentication code before sending the resulting encrypted authentication code to the second device 2 at step 302. The second device 2 can then decrypt the authentication code, and return the decrypted authentication code at step 308. Then, at step 312, the first device 1 can compare the original unencrypted authentication code with the decrypted authentication code. If the original unencrypted authentication code is equal to the decrypted authentication code, the second device 2 is successfully authenticated. Alternatively, the first device 1 can send an unencrypted authentication code to the second device 2 at step 302. The second device 2 can then encrypt the authentication code, and return the encrypted authentication code at step 308. Then, at step 312, the first device 1 can decrypt the authentication code, and compare the unencrypted authentication code with the decrypted authentication code. If the unencrypted authentication code is equal to the decrypted authentication code, the second device 2 is successfully authenticated.

In one example, a public-key cryptography system may be used. In this example, each second device 2 comprises its own unique private key, and the first device 1 comprises the corresponding public key for each second device 2 that is approved for use with the first device 1. The private key can be stored in a memory of the second device 2 during its manufacture. The public keys can be stored in a memory of the first device 1 during its manufacture, or can be downloaded from a secure server via a communication network. The first device 1 can encrypt the authentication code with the public key for the second device 2, before sending the resulting encrypted authentication code to the second device 2 at step 302. The second device 2 can then decrypt the authentication code with its private key, and return the decrypted authentication code at step 308. Then, at step 312, the control layer 8 can compare the original unencrypted authentication code with the decrypted authentication code. If the original unencrypted authentication code is equal to the decrypted authentication code, the second device 2 is successfully authenticated. This public-key authentication method has the advantage that, because each second device 2 has a unique private key, the integrity and security of the system as a whole is maintained even if the private key of one or more second devices 2 is compromised (e.g. by reverse engineering).

As another example, a symmetric key cryptography system may be used. In this example, the first device 1 and each second device 2 comprise the same symmetric key. The symmetric key can be stored in the memory of each device 1, 2 during manufacture. The first device 1 can encrypt the authentication code with the symmetric key, before sending the resulting encrypted authentication code to the second device 2 at step 302. The second device 2 can then decrypt the encrypted authentication code using the same symmetric key, and return the decrypted authentication code at step 308. Then, at step 312, the control layer 8 can compare the original unencrypted authentication code with the decrypted authentication code. If the original unencrypted authentication code is equal to the decrypted authentication code, the second device 2 is successfully authenticated. Variations on the previously-mentioned public-key and symmetric key techniques may be used and/or other cryptographic techniques may alternatively or additionally be used.

The authentication method 300 can enable a first device 1 (e.g. a radiotherapy device) to determine whether the second device 2 (e.g. an accessory) is genuine or otherwise approved for use with the first device 1. The method 300 thus aims to reduce the risks to health and safety that might result from the first device 1 being used with an unapproved second device 2. By disabling the functionality of the first device 1 when the second device 2 fails authentication, the device controller 10 can prevent the health and safety risks that may result from operating the first device 1 with an unapproved—and potentially unsafe—second device 2 connected thereto. This is particularly advantageous when the first device 1 is a radiotherapy device, because the use of an accessory that has not been approved by the manufacturer of the radiotherapy device may pose significant risks to a patient's wellbeing.

The method 300 has the additional advantage that it allows authentication capabilities to be added to the first device 1 without requiring any modification to the hardware layer 7 of its first interface 4. The authentication method 300 can be implemented simply by adding a second interface 6 to the first device 1, and by updating the instructions that are executed by the control layer 8 and the device controller 10. The first device 1 can thus be easily upgraded to authenticate a second device 2.

The methods disclosed herein can be performed by instructions stored on a processor-readable medium. The processor-readable medium may be: a read-only memory (including a PROM, EPROM or EEPROM); random access memory; a flash memory; an electrical, electromagnetic or optical signal; a magnetic, optical or magneto-optical storage medium; one or more registers of a processor; or any other type of processor-readable medium. In alternative embodiments, the present disclosure can be implemented as control logic in hardware, firmware, software or any combination thereof. The apparatus may be implemented by dedicated hardware, such as one or more application-specific integrated circuits (ASICs) or appropriately connected discrete logic gates. A suitable hardware description language can be used to implement the method described herein with dedicated hardware.

It will be understood that the embodiments have been described above purely by way of example, and that modifications of detail can be made within the scope of this disclosure. A true scope of the invention is indicated by the following claims and their equivalents.

The invention claimed is:

1. A radiotherapy device configured to identify an accessory for attachment to the device, the device comprising:
a first device interface configured to communicate with a first accessory interface of the accessory;
a second device interface configured to communicate with a second accessory interface of the accessory, the first device interface being distinct from the second device interface; and
one or more controllers configured to receive a first identifier from the first accessory interface via the first device interface, determine whether the first identifier has a predetermined value, upon determining that the first identifier has the predetermined value, receive a second identifier from the second accessory interface via the second device interface, identify the accessory using the second identifier, and transmit a control signal to the accessory based upon the identification of the accessory.

2. A device in accordance with claim 1, wherein the one or more controllers are further configured to authenticate the accessory by:

sending an authentication code to the accessory via the second device interface; and receiving the authentication code from the accessory via the first device interface.

3. A device in accordance with claim 1, wherein the first device interface is configured to allow communication between the device and the accessory via an electrical connection therebetween.

4. A device in accordance with claim 1, wherein the one or more controllers are further configured to control the functionality of the accessory by sending data to the accessory via the second device interface.

5. A device in accordance with claim 1, wherein the second device interface is configured to allow communication between the device and the accessory via a wireless communication link therebetween.

6. A device in accordance with claim 5, wherein the one or more controllers are further configured to extract the second identifier from a signal that is repeatedly broadcast by the accessory.

7. A device in accordance with claim 1, wherein upon determining that the first identifier has the predetermined value, the one or more controllers are further configured to transmit an actuation signal to the accessory, the actuation signal controlling the accessory to begin broadcasting the second identifier.

8. An accessory for a radiotherapy device, the accessory comprising:

a first accessory interface configured to communicate with a first device interface of the radiotherapy device;

a second accessory interface configured to communicate with a second device interface of the radiotherapy device, the first accessory interface being distinct from the second accessory interface; and one or more controllers configured to send a first identifier to the first device interface via the first accessory interface, the first identifier having a predetermined value, and send a second identifier to the second device interface via the second accessory interface, the second identifier having a value that identifies the accessory.

9. An accessory in accordance with claim 8, the one or more controllers being further configured to:

receive an authentication code from the radiotherapy device via the second accessory interface; and send the authentication code to the radiotherapy device via the first accessory interface.

10. An accessory in accordance with claim 8, wherein the first accessory interface is configured to allow communication between the radiotherapy device and the accessory via an electrical connection therebetween.

11. An accessory in accordance with claim 8, wherein the one or more controllers are further configured to:

receive data for controlling the functionality of the accessory from the radiotherapy device via the second accessory interface; and control the functionality of the accessory in accordance with the received data.

12. An accessory in accordance with claim 8, wherein the second accessory interface is configured to allow communication between the radiotherapy device and the accessory via a wireless communication link therebetween.

13. An accessory in accordance with claim 12, wherein the second accessory interface is configured to broadcast the second identifier repeatedly.

14. An accessory in accordance with claim 8, wherein the one or more controllers are further configured to begin broadcasting the second identifier upon receiving an actuation signal from the radiotherapy device.

15. A computer-implemented method for enabling a radiotherapy device to identify an accessory for attachment to the radiotherapy device, the method being performed by a processor of the radiotherapy device, the radiotherapy device comprising a first device interface configured to communicate with a first accessory interface of the accessory and a second device interface configured to communicate with a second accessory interface of the accessory, the first device interface being distinct from the second device interface, and wherein the method comprises:

receiving a first identifier from the first accessory interface via the first device interface;

determining whether the first identifier has a predetermined value;

upon determining that the first identifier has the predetermined value, receiving a second identifier from the second accessory interface via the second device interface;

identifying the accessory using the second identifier; and transmitting a control signal to the accessory based upon the identification of the accessory.

16. A method in accordance with claim 15, further comprising authenticating the accessory by:

sending an authentication code to the accessory via the second device interface; and receiving the authentication code from the accessory via the first device interface.

17. A method in accordance with claim 15, wherein the second device interface is configured to allow communication between the radiotherapy device and the accessory via a wireless communication link therebetween.

18. A computer-implemented method for enabling an accessory for a radiotherapy device to be identified by the radiotherapy device, the method being performed by a processor of the accessory, the accessory comprising a first accessory interface configured to communicate with a first device interface of the radiotherapy device and a second interface configured to communicate with a second device interface of the radiotherapy device, the first accessory interface being distinct from the second accessory interface, and wherein the method comprises:

sending a first identifier to the first device interface via the first accessory interface, the first identifier having a predetermined value; and sending a second identifier to the second device interface via the second accessory interface, the second identifier having a value that identifies the accessory.

19. A method in accordance with claim 18, further comprising:

receiving an authentication code from the radiotherapy device via the second accessory interface; and sending the authentication code to the radiotherapy device via the first accessory interface.

20. A method in accordance with claim 18, further comprising:
receiving data for controlling the functionality of the accessory from the radiotherapy device via the second accessory interface; and
controlling the functionality of the accessory in accordance with the received data.

* * * * *